US006281303B1

(12) United States Patent
Lavoie et al.

(10) Patent No.: US 6,281,303 B1
(45) Date of Patent: Aug. 28, 2001

(54) OLEFIN OLIGOMERIZATION AND POLYMERIZATION CATALYSTS

(75) Inventors: Gino Georges Lavoie; James Allen Ponasik, Jr., both of Kingsport; Christopher Moore Killian, Gray; Leslie Shane Moody, Johnson City; Peter Borden Mackenzie, Kingsport, all of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/361,752

(22) Filed: Jul. 27, 1999

(51) Int. Cl.[7] ............................. C08F 4/26; C08F 10/02; C08F 210/02
(52) U.S. Cl. ................. 526/127; 526/172; 526/348.6; 526/352; 502/155
(58) Field of Search ................. 526/172, 348.6, 526/348, 352, 129, 127; 502/155

(56) References Cited

U.S. PATENT DOCUMENTS

| 4,689,437 | 8/1987 | Murray . |
| 4,691,036 | 9/1987 | Starzewski et al. . |
| 4,716,138 | 12/1987 | Murray . |
| 4,716,205 | 12/1987 | Klabunde . |
| 4,724,273 | 2/1988 | Fink et al. . |
| 4,906,754 | 3/1990 | Klabunde . |
| 5,030,606 | 7/1991 | Klabunde . |
| 5,175,326 | 12/1992 | Klabunde . |
| 6,037,297 | * 3/2000 | Stibrany et al. ............ 502/155 |
| 6,060,569 | * 5/2000 | Bennett et al. ............ 526/172 |

FOREIGN PATENT DOCUMENTS

| 381495 | 8/1990 | (EP) . |
| 96-70332 | 9/1997 | (JP) . |
| 96-84343 | 10/1997 | (JP) . |
| 96-84344 | 10/1997 | (JP) . |
| WO 96/23010 | 8/1996 | (WO) . |
| WO 97/02298 | 1/1997 | (WO) . |
| WO 97/17380 | 5/1997 | (WO) . |
| WO 97/38024 | 10/1997 | (WO) . |
| WO 97/48735 | 12/1997 | (WO) . |
| WO 97/48736 | 12/1997 | (WO) . |
| WO 97/48737 | 12/1997 | (WO) . |
| WO 97/48742 | 12/1997 | (WO) . |
| WO 98/03521 | 1/1998 | (WO) . |
| WO 98/03559 | 1/1998 | (WO) . |
| WO 98/27124 | 6/1998 | (WO) . |
| WO 98/30612 | 7/1998 | (WO) . |
| WO 98/37110 | 8/1998 | (WO) . |
| WO 98/40374 | 9/1998 | (WO) . |
| WO 98/40420 | 9/1998 | (WO) . |
| WO 98/47933 | 10/1998 | (WO) . |
| WO 99/02472 | 1/1999 | (WO) . |
| WO 99/12981 | 3/1999 | (WO) . |

OTHER PUBLICATIONS

L. K. Johnson et al., J. Am. Chem. Soc., 1995, 117, 6414–6415.
G. F. Schmidt et al., J. Am. Chem. Soc. 1985, 107, 1443–1444.
M. Brookhart et al., Macromolecules, 1995, 28, 5378–5380.
M. Peuckert et al., Organometallics, 1983, 2(5), 594–597.
W. Keim et al., Angew. Chem. Int. Ed. Eng., 20, 1981, No. 1, 116–117.
V. M. Mohring et al., Angew. Chem. Int. Ed. Eng., 24, 1985, 1001–1003.
G. Wilke, Angew. Chem. Int. Ed. Engl., 1988, 27, 185–206.
K. A. O. Starzewski et al., Angew. Chem. Int. Ed. Engl., 26, 1987, 63–64.
B. L. Small et al., J. Am. Chem. Soc., 120, No. 16, 1998, 4049–4050.
B. L. Small et al., J. Am. Chem. Soc., 1998, 120, 7143–7144.
G. J. P. Britovsek et al., Chem. Commun., 1998, 849–850.
U. Klabunde et al., J. Mol Cat., 41, 1987, 123–134.
C. Pellecchia et al., Macromol. Rapid Commun. 19, No. 12, 651–655 (1998).
G. Britovsek et al., J. Am. Chem. Soc. 1999, 121, 8728–8740.

* cited by examiner

Primary Examiner—David W. Wu
Assistant Examiner—R. Harlan
(74) Attorney, Agent, or Firm—Jonathan D. Wood; Bernard J. Graves, Jr.

(57) ABSTRACT

Disclosed herein are compounds and processes useful for the oligomerization and polymerization of olefins. Transition metal catalyst complexes of groups 7 through 10 with tridentate ligands are described, along with a representative polymerization of ethylene using one of the cobalt complexes. The transition metal complexes of the invention may also be attached to a solid support and used in gas phase processes.

34 Claims, No Drawings

OLEFIN OLIGOMERIZATION AND POLYMERIZATION CATALYSTS

FIELD OF THE INVENTION

This invention provides a class of olefin oligomerization and polymerization catalysts based on cobalt, iron, ruthenium and manganese complexes of tridentate ligands. In a preferred embodiment the catalyst systems also comprise a Lewis or Bronsted acid. Also provided is a process for the preparation of polyolefins.

BACKGROUND OF THE INVENTION

Olefin polymers are used in a wide variety of products, from sheathing for wire and cable to film. Olefin polymers are used, for instance, in injection or compression molding applications, in extruded films or sheeting, as extrusion coatings on paper, for example photographic paper and digital recording paper, and the like. Improvements in catalysts have made it possible to better control polymerization processes, and thus influence the properties of the bulk material. Increasingly, efforts are being made to tune the physical properties of plastics for lightness, strength, resistance to corrosion, permeability, optical properties, and the like, for particular uses. Chain length, polymer branching and functionality have a significant impact on the physical properties of the polymer. Accordingly, novel catalysts are constantly being sought in attempts to obtain a catalytic process for polymerizing olefins which permits more efficient and better controlled polymerization of olefins.

Conventional polyolefins are prepared by a variety of polymerization techniques, including homogeneous liquid phase, gas phase, and slurry polymerization. Certain transition metal catalysts, such as those based on titanium compounds (e.g. $TiCl_3$ or $TiCl_4$) in combination with organoaluminum cocatalysts, are used to make linear and linear low density polyethylenes as well as poly-$\alpha$-olefins such as polypropylene. These so-called "Ziegler-Natta" catalysts are quite sensitive to oxygen and are ineffective for the copolymerization of nonpolar and polar monomers.

In contrast to the volumes of work describing early metal group 4–6 olefin oligomerization and polymerization catalysts, there have been relatively few reports of group 7–10 catalysts for the polymerization of olefins. WO 96/23010 describes the polymerization of olefins using cationic nickel, palladium, iron, and cobalt complexes containing diimine and bisoxazoline ligands.

WO 96/23010 also describes a series of novel polyolefins based on ethylene homopolymer and copolymers, as well as homo- and copolymers of alpha-olefins including propylene, 1-hexene, and methylacrylate among others. WO 97/02298 further complements WO 96/23010 by describing other possible ligands coordinated to nickel and the use of the corresponding complexes in the polymerization of alkenes. See also, WO 98/47933, WO 98/40420, WO 98/40374, and WO 98/37110.

European Patent Application Serial No. 381,495 describes the polymerization of olefins using palladium and nickel catalysts which contain selected bidentate phosphorous containing ligands.

L. K. Johnson et al., *J. Am. Chem. Soc.*, 1995, 117, 6414, describe the polymerization of olefins such as ethylene, propylene, and 1-hexene using cationic $\alpha$-diimine-based nickel and palladium complexes. These catalysts have been described to polymerize ethylene to high molecular weight branched polyethylene. In addition to ethylene, Pd complexes act as catalysts for the polymerization and copolymerization of olefins and methyl acrylate.

G. F. Schmidt et al., *J. Am. Chem. Soc.* 1985, 107,1443, describe a cobalt(III) cyclopentadienyl catalytic system having the structure $[C_5Me_5(L^*)CoCH_2CH_2\text{-}\mu\text{-}H]^+$, which provides for the "living" polymerization of ethylene.

M. Brookhart et al., *Macromolecules* 1995, 28, 5378, disclose using such "living" catalysts in the synthesis of end-functionalized polyethylene homopolymers.

U. Klabunde, U.S. Pat. Nos. 4,906,754, 4,716,205, 5,030,606, and 5,175,326, describes the conversion of ethylene to polyethylene using anionic phosphorous, oxygen donors ligated to Ni(II). The polymerization reactions were run between 25 and 100° C. with modest yields, producing linear polyethylene having a weight-average molecular weight ranging between 8K and 350 K. In addition, Klabunde describes the preparation of copolymers of ethylene and functional group containing monomers.

M. Peuckert et al., *Organomet.* 1983, 2(5), 594, disclose the oligomerization of ethylene using phosphine, carboxylate donors ligated to Ni(II), which showed modest catalytic activity (0.14 to 1.83 TO/s). The oligomerizations were carried out at 60 to 95° C. and 10 to 80 bar ethylene in toluene, to produce $\alpha$-olefins.

R. E. Murray, U.S. Pat. Nos. 4,689,437 and 4,716,138, describes the oligomerization of ethylene using phosphine, sulfonate donors ligated to Ni(II). These complexes show catalyst activities approximately 15 times greater than those reported with phosphine, carboxylate analogs.

W. Keim et al., *Angew. Chem. Int. Ed. Eng.* 1981, 20,116, and V. M. Mohring, et al., *Angew. Chem. Int. Ed. Eng.* 1985, 24,1001, disclose the polymerization of ethylene and the oligomerization of $\alpha$-olefins with aminobis(imino) phosphorane nickel catalysts; G. Wilke, *Angew. Chem. Int. Ed. Engl.* 1988, 27, 185, describes a nickel allyl phosphine complex for the polymerization of ethylene.

K. A. O. Starzewski et al., *Angew. Chem. Int. Ed. Engl.* 1987, 26, 63, and U.S. Pat. No. 4,691,036, describe a series of bis(ylide) nickel complexes, used to polymerize ethylene to provide high molecular weight linear polyethylene.

WO Patent Application 97/02298 discloses the polymerization of olefins using a variety of neutral N, O, P, or S donor ligands, in combination with a nickel(0) compound and an acid.

Brown et al., WO 97/17380, describes the use of Pd $\alpha$-diimine catalysts for the polymerization of olefins including ethylene in the presence of air and moisture.

Fink et al., U.S. Pat. No. 4,724,273, have described the polymerization of $\alpha$-olefins using aminobis(imino) phosphorane nickel catalysts and the compositions of the resulting poly($\alpha$-olefins).

Recently Vaughan et al. WO 9748736, Denton et al. WO 9748742, and Sugimura et al. WO 9738024 have described the polymerization of ethylene using silica supported $\alpha$-diimine nickel catalysts.

Additional recent developments are described by Sugimura et al., in JP96-84344, JP96-84343, by Yorisue et al., in JP96-70332, by Canich et al. WO 9748735, McLain et al. WO 9803559, Weinberg et al. WO 9803521 and by Matsunaga et al. WO 9748737.

Cobalt(II) and iron(II) complexes with coordinated 2,6-bisiminopyridine ligands were independently reported by Brookhart at the University of North Carolina in collaboration with DuPont (Small, B. L.; Brookhart, M.; Benneth, A. M. A. *J. Am. Chem. Soc.* 1998, 120, 4049; Small, B. L.;

Brookhart, M. *J. Am. Chem. Soc.* 1998, 120, 7143) and by Gibson at Imperial College in collaboration with BP Chemicals (Britovsek, G. J. P. et al. *Chem. Commun.* 1998, 849). Upon activation with modified methylaluminoxane, those catalysts polymerize ethylene in good rate. The iron complexes could also polymerize propylene with a number average molecular weight consistently higher than 5000. The polypropylene thus obtained was found to be mainly isotactic. (See also WO 99/02472, 98/27124 and WO 98/30612).

Brookhart and coworkers have also described a cobalt(III) cyclopentadienyl system of the general structure [$C_5Me_5$(L*)$CoCH_2CH_2$-$\mu$-H]$^+$ (Schmidt, G. F.; Brookhart, M. *J. Am. Chem. Soc.* 1985, 107,1443). These catalysts effect the "living" polymerization of ethylene. The living nature of these catalysts has been exploited for the synthesis of end-functionalized polyethylene homopolymers (Brookhart, M.; DeSimone, J. M.; Grant, B. E.; Tanner, M. J. *Macromolecules* 1995, 28, 5378).

Klabunde and Ittel from DuPont reported the conversion of ethylene to polyethylene using phosphorous/oxygen chelate ligands. The polymerization reactions were run between 25 and 100° C. with modest productivities resulting in linear polyethylene having a weight average molecular weight ranging between 8K and 350K. (Klabunde, U.; Ittel, S. D. *J. Mol. Cat.* 1987, 41,123–134.)

The polymerization of ethylene and the oligomerization of α-olefins with aminobis(imino)phosphorane-nickel catalysts have also been described. (Keim, W.; Appel, R.; Storeck, A.; Kruger, C.; Goddard, R. *Angew. Chem. Int. Ed. Eng.* 1981, 20,116. Mohring, V. M.; Fink, G. *Angew. Chem. Int. Ed. Eng.* 1985, 24,1001). Other group 10 catalysts known in the art include a nickel allyl phosphine complex described by Wilke (Wilke, G. *Angew. Chem. Int. Ed. Engl.* 1988, 27, 185), and a series of bis(ylide) nickel complexes which are reported by K. Alexander Ostoja Starzewski to polymerize ethylene to high molecular weight linear polyethylene. (Starzewski, K. A. O.; Witte, J. *Angew. Chem. Int. Ed. Engl.* 1987, 26, 63.).

SUMMARY OF THE INVENTION

This invention provides a process for the preparation of polyolefins, which comprises contacting one or more monomers of the formula R'CH=CHR" with a transition metal complex of the formula (I):

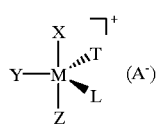

wherein X, Y, and Z are selected from various functional groups or combinations of such functional groups as depicted below;

R', R" are H, hydrocarbyl or substituted hydrocarbyl, and may be linked to form a cyclic olefin;

T is H, hydrocarbyl, substituted hydrocarbyl, or other group capable of inserting an olefin;

L is an olefin or a neutral base where the donating atom is nitrogen, oxygen, or sulfur capable of being displaced by an olefin; in addition, T and L may be taken together to form, for example, a π-allyl or a π-benzyl group;

M is Co(II), Co(III), Fe(II), Fe(III), Ru(II), Ru(III), Mn(II) or Mn(III); and

A$^-$ is a weakly coordinating anion.

As a further aspect of the invention, there is provided a process for the polymerization of olefins which comprises contacting one or more monomers of the formula R'CH=CHR" with a transition metal catalyst, wherein said catalyst is formed by combining a first compound D, which is a neutral Lewis acid that is capable of abstracting Q$^-$ or W$^-$ to form a weakly coordinating anion, or a cationic Lewis acid whose counterion is a weakly coordinating anion, or a Bronsted acid whose conjugate base is a weakly coordinating anion, with a second compound of the formula (II):

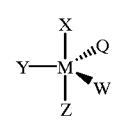

wherein X, Y, and Z are selected from various functional groups or combinations of such functional groups as depicted below;

R', R" are H, hydrocarbyl or substituted hydrocarbyl, and may be linked to form a cyclic olefin;

Q is hydrocarbyl, chloride, iodide, bromide, substituted hydrocarbyl, hydroxide, alkoxide, amide, nitrate or sulphonate or other group capable of being abstracted by a compound D, which is a neutral Lewis acid that is capable of abstracting Q$^-$ or W$^-$ to form a weakly coordinating anion, or a cationic Lewis acid whose counterion is a weakly coordinating anion, or a Brønsted acid whose conjugate base is a weakly coordinating anion;

W is H, hydrocarbyl, chloride, iodide, bromide, substituted hydrocarbyl, hydroxide, alkoxide, amide, nitrate or sulphonate or other group capable of inserting an olefin; and, M is Co(II), Co(III), Fe(II), Fe(III), Ru(II), Ru(III), Mn(II) or Mn(III).

In the above processes, the temperature at which the process is conducted will be limited by the inherent thermal stability of the catalysts. In this regard, it is preferred that the process be conducted at a temperature of from about 25 to 150° C. and more preferably from about 50 to 100° C. Further, no specific geometric isomer is intended by the depiction of the catalysts herein.

DETAILED DESCRIPTION OF THE INVENTION

In a preferred embodiment, the present invention provides a process for the preparation of polyolefins, which comprises contacting one or more monomers of the formula R'CH=CHR" with a transition metal complex of the formula (I):

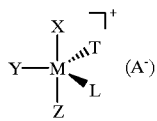

wherein R', R" are H, hydrocarbyl or substituted hydrocarbyl, and may be linked to form a cyclic olefin;

M is Co(II), Co(III), Fe(II), Fe(III), Ru(II), Ru(III), Mn(II) or Mn(III);

T is H, hydrocarbyl, substituted hydrocarbyl, or other group capable of inserting an olefin;

L is an olefin or a neutral base where the donating atom is nitrogen, oxygen, or sulfur capable of being displaced by an olefin; in addition, T and L may be taken together to form a π-allyl or a π-benzyl group;

A⁻ is a weakly coordinating anion; and

X, Y, and Z are selected from various functional groups or combinations of such functional groups selected from

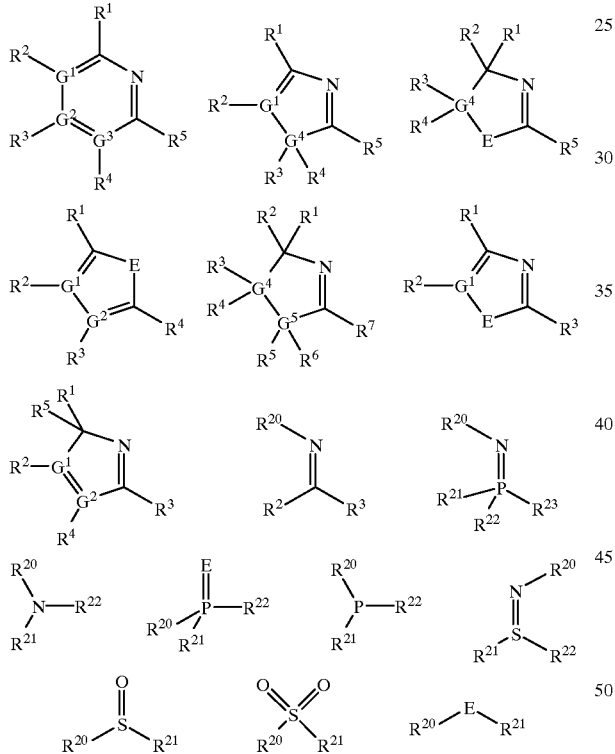

wherein $R^1$, $R^2$, $R^3$, $R^4$, are each independently H, substituted substituted hydrocarbyl, a heteroatom connected monoradical wherein the connected heteroatom is selected from Group 15 or 16, or silyl, and may also be linked by a bridging hydrocarbyl group or to one another or to $R^{20}$–$R^{23}$ to form a covalent bond;

$R^{20}$, $R^{21}$, $R^{22}$, and $R^{23}$ are each independently hydrocarbyl, substituted hydrocarbyl or silyl, and may also be linked to $R^1$–$R^7$ to form a covalent bond;

E is O or S;

$G^1$, $G^2$, and $G^3$ are each independently C or N, provided that when $G^1$, $G^2$, and $G^3$ are N, only hydrocarbyl and substituted hydrocarbyl substituents are covalently bound to N, and further provided that the octet rule is satisfied in said atom;

$G^4$ and $G^5$ are independently C, N, O, or S, provided that when they are O, N, and S, only hydrocarbyl and substituted hydrocarbyl substituents are covalently bound to O, N or S, and further provided that the octet rule is satisfied in said atom;

further provided that when M is either Mn(I), Mn(II), Mn(III), Mn(IV), Co(I), Co(II), Co(III), Fe(II), Fe(III), Ru(II), Ru(III) or Ru(IV), X, Y and Z are taken together to form groups of a formula other than the formula

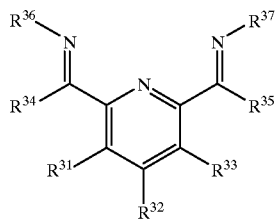

wherein $R^{31}$, $R^{32}$, $R^{33}$, $R^{34}$ and $R^{35}$ are each independently H, hydrocarbyl, substituted hydrocarbyl, heterohydrocarbyl, or substituted heterohydrocarbyl, or an inert functional group; and $R^{36}$ and $R^{37}$ are aryl, substituted aryl, H, halogen, hydrocarbyl, substituted hydrocarbyl, heterohydrocarbyl, or substituted heterohydrocarbyl.

In this regard, $R^{31}$ through $R^{37}$ are intended to be defined as used in WO 98/27124, WO 98/30612, and WO99112981.

As used herein, the "octet rule" refers to the principle that, except for hydrogen, an atom combines with other atoms in a covalent bond in order to have eight electrons in its valence shell.

Preferably, M is a metal in the +2 oxidation state, although metals in the +3 oxidation state can be utilized.

The X, Y and Z groups may be used as independent parts of the complex, or may be linked directly to one another via a covalent bond by using two of $R^1$, $R^2$, $R^3$, $R^4$, $R^5$, $R^6$, $R^7$, and $R^{20-23}$ to form a bidentate ligand (XY) where Z would be used as a monodentate component, provided that $R^{20-23}$ are not used to link together two heteroatoms, e.g., a —N—N— linkage. Alternatively, and preferably, X, Y and Z may be linked directly to one another via covalent bonds using two of $R^1$, $R^2$, $R^3$, $R^4$, $R^5$, $R^6$, $R^7$, and $R^{20-23}$, provided that $R^{20-23}$ are not used to link together two heteroatoms to form a tridentate ligand (XYZ), which is in turn ligated to M via N, O, P or S atom(s).

Preferred ligands of the formula X-Y-Z include the following:

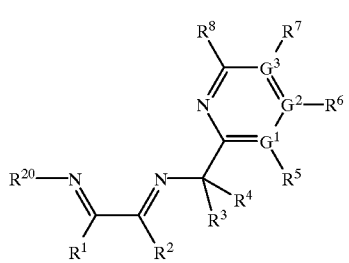

CI
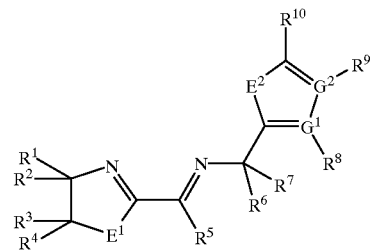
CII
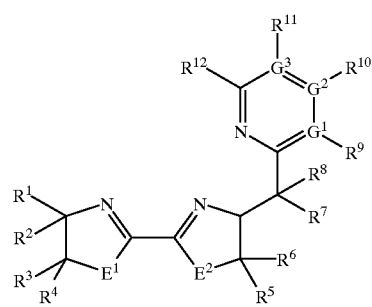
CIII
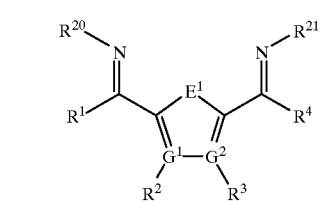
CIV
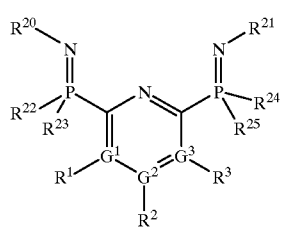
CV
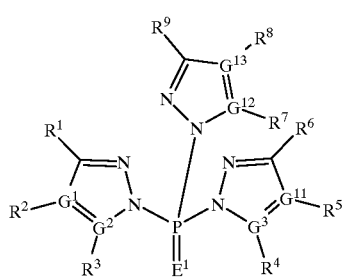
CVII
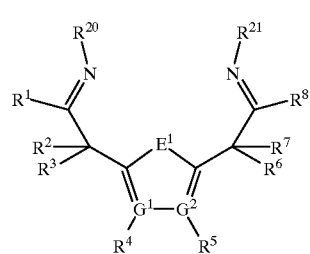
CVIII
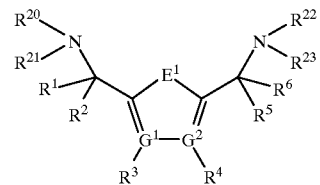
CIX
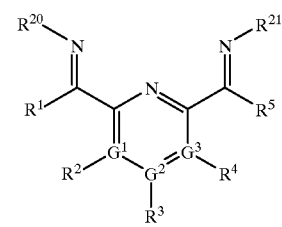
CXI
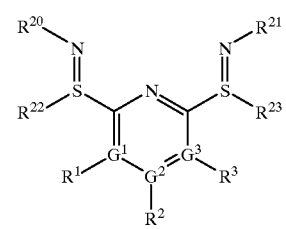
CXII
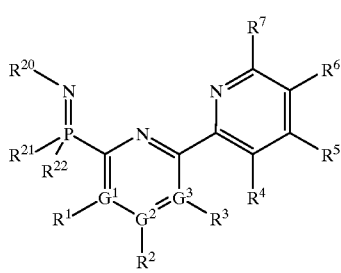
CXIII
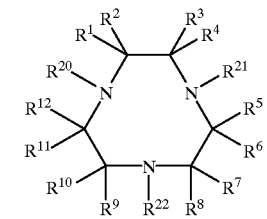
CXIV
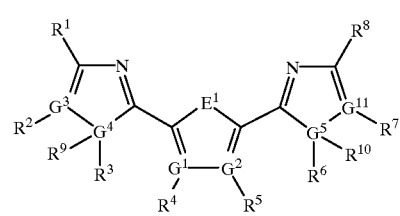

CXV

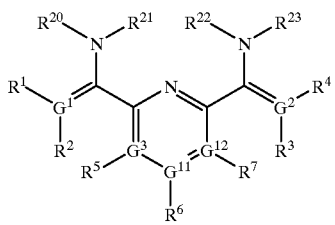

CXVI

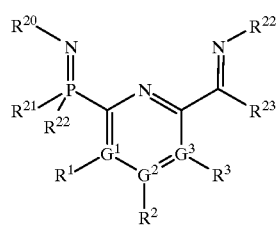

wherein R¹–R¹⁵ are each independently H, hydrocarbyl, substituted hydrocarbyl, a heteroatom connected monoradical wherein the connected heteroatom is selected from Group 15 and 16, or silyl, and may also be linked by a bridging hydrocarbyl group or to one another or to R²⁰–R²³ to form a covalent bond;

R²⁰, R²¹, R²², and R²³ are each independently hydrocarbyl, substituted hydrocarbyl or silyl, and may also be linked to R¹–R⁷ to form a covalent bond;

and E¹ and E² are each independently either O or S;

G¹, G², G³, G¹¹, G¹² and G¹³ are each independently C or N, provided that when they are N, only hydrocarbyl and substituted hydrocarbyl subtituents are covalently bound to N, and further provided that the octet rule is satisfied in said atom;

G⁴ and G⁵ are each independently C, N, O, or S, provided that when G⁴ and

G⁵ are O, N, and S, only hydrocarbyl and substituted hydrocarbyl substituents are covalently bound to O, N or S, and further provided that the octet rule is satisfied in said atom.

Further preferred ligands include those wherein at least one of the X, Y and Z units is chosen to be

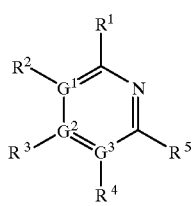

while remaining units are chosen among the following:

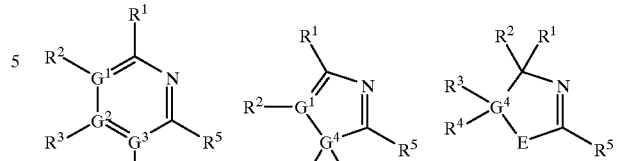

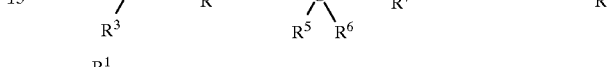

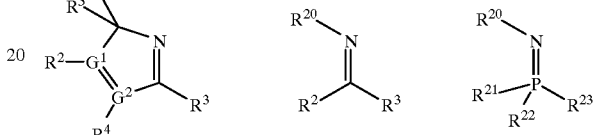

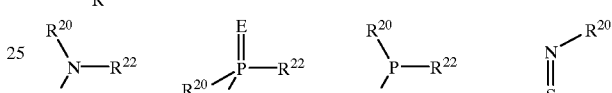

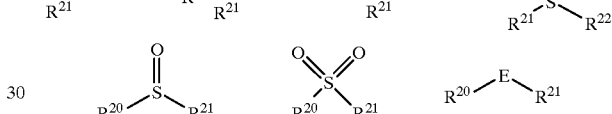

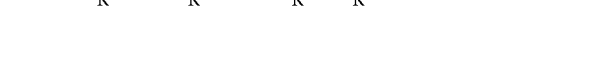

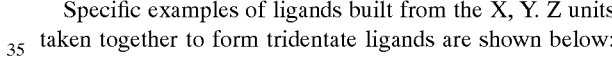

Specific examples of ligands built from the X, Y, Z units taken together to form tridentate ligands are shown below:

L

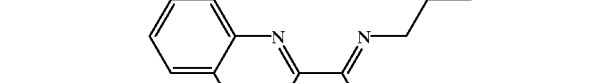

LI

LII

-continued
LIII
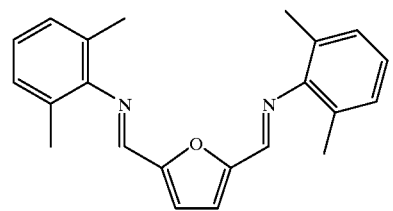
LIV
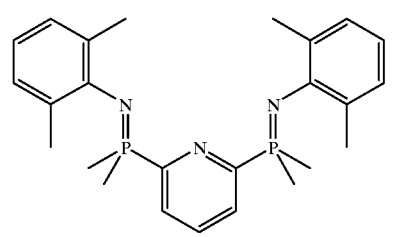
LV
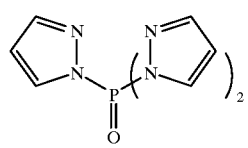
LVI
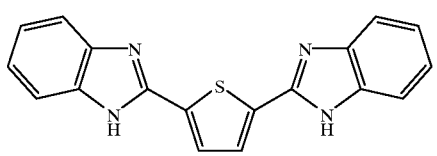
LVIII
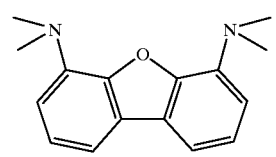
LVIX
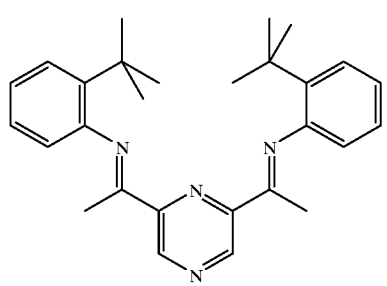
LVII
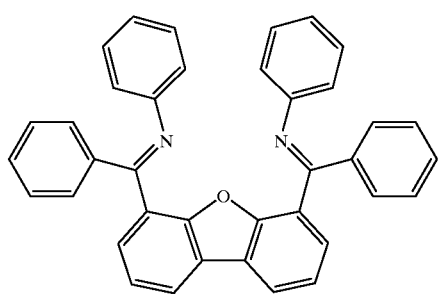
-continued
LX
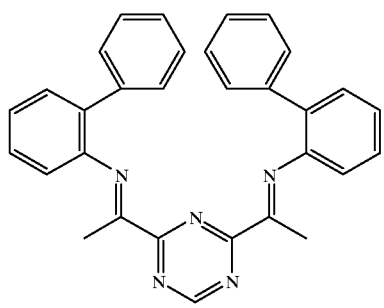
LXI
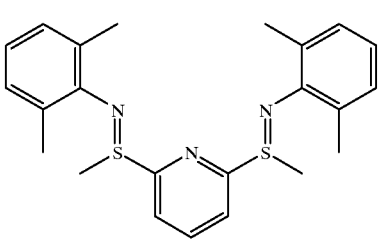
LXII
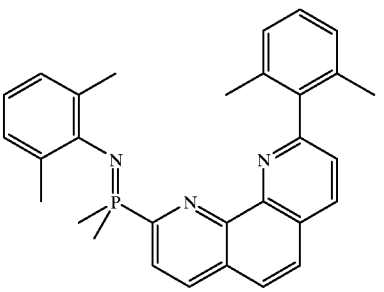
LXIII
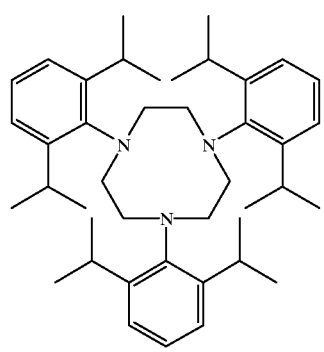
LXIV

LXV

LXVI

As a further aspect of the invention, there are provided the above compounds of Formula I, provided that when M is either Mn(I), Mn(II), Mn(III), Mn(IV), Co(I), Co(II), Co(III), Fe(II), Fe(III), Ru(II), Ru(III) or Ru(IV), X, Y and Z are taken together to form groups of a formula other than the formula wherein $R^{31}$, $R^{32}$, $R^{33}$, $R^{34}$ and $R^{35}$ are each independently H, hydrocarbyl, substituted hydrocarbyl, heterohydrocarbyl, or substituted heterohydrocarbyl, or an inert functional group; and $R^{36}$ and $R^{37}$ are aryl, substituted aryl, H, halogen, hydrocarbyl, substituted hydrocarbyl, heterohydrocarbyl, or substituted heterohydrocarbyl.

In a further preferred embodiment, the catalysts of the invention are attached to a solid support.

As a further aspect of the invention, there is provided a process for the polymerization of olefins which comprises contacting one or more monomers of the formula R'CH=CHR" with transition metal catalyst, wherein said catalyst is formed by combining a first compound D, which is a neutral Lewis acid that is capable of abstracting Q⁻ or W⁻ to form a weakly coordinating anion, or a cationic Lewis acid whose counterion is a weakly coordinating anion, or a Brønsted acid whose conjugate base is a weakly coordinating anion, with a second compound of the formula (II):

II wherein R', R" are H, hydrocarbyl or substituted hydrocarbyl, and may be linked to form a cyclic olefin;

Q is hydrocarbyl, chloride, iodide, bromide, substituted hydrocarbyl, hydroxide, alkoxide, amide, nitrate or sulphonate or other group capable of being abstracted by compound D, which is a neutral Lewis acid that is capable of abstracting Q⁻ or W⁻ to form a weakly coordinating anion, or a cationic Lewis acid whose counterion is a weakly coordinating anion, or a Brønsted acid whose conjugate base is a weakly coordinating anion;

W is hydrocarbyl, chloride, iodide, bromide, substituted hydrocarbyl, hydroxide, alkoxide, amide, nitrate or sulphonate or other group capable of inserting an olefin;

M is Co(II), Co(III), Fe(II), Fe(III), Ru(II), Ru(III), Mn(II) or Mn(III); and

X, Y, and Z are selected from various functional groups or combinations of such functional groups selected from wherein $R^1$, $R^2$, $R^3$, $R^4$, $R^5$, $R^6$, $R^7$ are each independently H, hydrocarbyl, substituted hydrocarbyl, a heteroatom connected monoradical wherein the connected heteroatom is selected from Group 15 and 16, or silyl, and may also be linked by a bridging hydrocarbyl group or to one another or to $R^{20}$–$R^{23}$ to form a covalent bond;

$R^{20}$, $R^{21}$, $R^{22}$, and $R^{23}$ are each independently hydrocarbyl, substituted hydrocarbyl or silyl, and may also be linked to $R^1$–$R^7$ to form a covalent bond;

and E is either O or S;

and $G^1$, $G^2$, and $G^3$ are independently C or N, provided that when they are N, only hydrocarbyl and substituted hydrocarbyl subtituents are covalently bound to N, and further provided that the octet rule is satisfied in said atom;

$G^4$ and $G^5$ are independently C, N, O, or S, provided that when they are O, N, and S, only hydrocarbyl and substituted hydrocarbyl substituents are covalently bound to O, N or S, and further provided that the octet rule is satisfied in said atom;

provided that when M is either Mn(I), Mn(II), Mn(III), Mn(IV), Co(I), Co(II), Co(III), Fe(II), Fe(III), Ru(II), Ru(III) or Ru(IV), X, Y and Z are taken together to form groups of a formula other than the formula

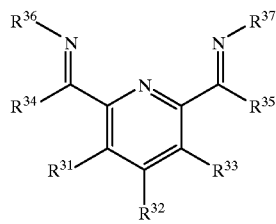

wherein $R^{31}$, $R^{32}$, $R^{33}$, $R^{34}$ and $R^{35}$ are each independently H, hydrocarbyl, substituted hydrocarbyl, heterohydrocarbyl, or substituted heterohydrocarbyl, or an inert functional group; and $R^{36}$ and $R^{37}$ are aryl, substituted aryl, H, halogen, hydrocarbyl, substituted hydrocarbyl, heterohydrocarbyl, or substituted heterohydrocarbyl.

The heterocyclic rings shown above may contain N, O or S atoms as shown by $G^1$–$G^3$ above, with corresponding changes in the substituents such that the octet rule is satisfied in said atom. The position of the double bonds in the heterocyclic rings is not restricted to the ones illustrated above. Tautomers are also intended to be covered by the above formulae.

In this disclosure certain chemical groups or compounds are described by certain terms and symbols. These terms are defined as follows:

Symbols ordinarily used to denote elements in the Periodic Table take their ordinary meaning, unless otherwise specified. Thus, N, O, S, P, and Si stand for nitrogen, oxygen, sulfur, phosphorus, and silicon, respectively.

The term "alkoxide" preferably refers to a $C_1$–$C_{12}$ straight or branched chain alkyloxy anion, optionally substitued by hydrocarbyl or substituted hydrocarbyl. Examples of such groups include methoxide, ethoxide, and the like.

Examples of neutral Lewis acids include, but are not limited to, methylaluminoxane (hereinafter MAO) and other aluminum sesquioxides, $R^{40}_3Al$, $R^{40}_2AlCl$, $R^{40}AlCl_2$ (where $R^{40}$ is alkyl), organoboron compounds, boron halides, $B(C_6F_5)_3$, $BPh_3$, and $B(3,5\text{-}(CF_3)_2C_6H_3)_3$. Examples of ionic compounds comprising a cationic Lewis acid include: $R^{41}_3Sn[BF_4]$, (where $R^{41}$ is hydrocarbyl), $MgCl_2$, and $H^+J^-$, where $J^-$ is a weakly coordinating anion.

The term "weakly coordinating anion" is well-known in the art per se and generally refers to a large bulky anion capable of delocalization of the negative charge of the anion. Suitable weakly coordinating anions, not all of which are bulky, include, but are not limited to, $PF_6^-$, $BF_4^-$, $SbF_6^-$, $(Ph)_4B^-$ wherein Ph=phenyl, $^-BAr_4$ wherein $^-BAr_4$=tetrakis[3,5-bis(trifluoromethyl)phenyl]borate. The coordinating ability of such anions is known and described in the literature (Strauss, S. et al., Chem. Rev. 1993, 93, 927).

Examples of neutral Lewis bases include, but are not limited to, (i) ethers, for example, diethyl ether or tetrahydrofuran, (ii) organic nitriles, for example acetonitrile, (iii) organic sulfides, for example dimethylsulfide, or (iv) monoolefins, for example, ethylene, hexene or cyclopentene.

A "hydrocarbyl" group means a monovalent or divalent, linear, branched or cyclic group which contains only carbon and hydrogen atoms. Examples of monovalent hydrocarbyls include the following: $C_1$–$C_{20}$ alkyl; $C_1$–$C_{20}$ alkyl substituted with one or more groups selected from C1–$C_{20}$ alkyl, $C_3$–$C_8$ cycloalkyl or aryl; $C_3$–$C_8$ cycloalkyl; $C_3$–$C_8$ cycloalkyl substituted with one or more groups selected from $C_1$–$C_{20}$ alkyl, $C_3$–$C_8$ cycloalkyl or aryl; $C_6$–$C_{14}$ aryl; and $C_6$–$C_{14}$ aryl substituted with one or more groups selected from $C_1$–$C_{20}$ alkyl, $C_3$–$C_8$ cycloalkyl or aryl; where the term "aryl" preferably denotes a phenyl, napthyl, or anthracenyl group. Examples of divalent (bridging) hydrocarbyls include: —$CH_2$—, —$CH_2CH_2$—, —$CH_2CH_2CH_2$—, and 1,2-phenylene.

A "silyl" group refers to a $SiR_3$ group wherein Si is silicon and R is hydrocarbyl or substituted hydrocarbyl or silyl, as in $Si(SiR_3)_3$.

A "heteroatom" refers to an atom other than carbon or hydrogen. Preferred heteroatoms include oxygen, nitrogen, phosphorus, sulfur, selenium, arsenic, chlorine, bromine, silicon and fluorine.

A "substituted hydrocarbyl" refers to a monovalent or divalent hydrocarbyl substituted with one or more heteroatoms. Examples of monovalent substituted hydrocarbyls include: 2,6-dimethyl4-methoxyphenyl, 2,6-diisopropyl-4-methoxyphenyl, 4-cyano-2,6-dimethylphenyl, 2,6-dimethyl-4-nitrophenyl, 2,6-difluorophenyl, 2,6-dibromophenyl, 2,6-dichlorophenyl, 4-methoxycarbonyl-2,6-dimethylphenyl, 2-tert-butyl-6-chlorophenyl, 2,6-dimethyl-4-phenylsulfonylphenyl, 2,6-dimethyl-4-trifluoromethylphenyl, 2,6-dimethyl-4-trimethylammoniumphenyl (associated with a weakly coordinated anion), 2,6-dimethyl-4-hydroxyphenyl, 9-hydroxyanthr-10-yl, 2-chloronapth-1-yl, 4-methoxyphenyl, 4-nitrophenyl, 9-nitroanthr-10-yl, —$CH_2OCH_3$, cyano, trifluoromethyl, or fluoroalkyl. Examples of divalent (bridging) substituted hydrocarbyls include: 4-methoxy-1,2-phenylene, 1-methoxymethyl-1,2-ethanediyl, 1,2-bis(benzyloxymethyl)-1,2-ethanediyl, or 1-(4-methoxyphenyl)-1,2-ethanediyl.

An "inert functional group" is a group other than hydrocarbyl or substituted hydrocarbyl which is inert under the process conditions to which the compound containing the group is subjected. The functional groups also do not substantially interfere with any process described herein or in WO 98/27124, that the compound in which they are present may take part in.

A "bridging hydrocarbyl group" refers to a divalent hydrocarbyl, divalent substituted hydrocarbyl, —C(O)—, —C(S)—, substituted silicon atom, substituted sulfur atom, substituted phosphorous atom, —$CH_2C(O)$—, —C(O)C(O)—, or 3,4,5,6-tetrafluoro-1,2-phenylene. A "substituted silicon atom" refers to a —$SiR^{90}_2$—group, wherein $R^{90}$ is a hydrocarbyl or substituted hydrocarbyl. A "substituted phosphorous atom" refers to a —$P(O)(OR^{90})$— group, wherein $R^{90}$ is a hydrocarbyl or substituted hydrocarbyl. A "substituted sulfur atom" refers to a —S(O)—, —$SO_2$—, or —$S(NR^{90})_2$—group, wherein $R^{90}$ is a hydrocarbyl or substituted hydrocarbyl.

A "mono-olefin" refers to a hydrocarbon containing one carbon—carbon double bond.

The term "polymer" as used herein is meant a species comprised of monomer units and having a degree of polymerization (DP) of ten or higher.

A "π-allyl" group refers to a monoanionic group with three $sp^2$ carbon atoms bound to a metal center in a $\eta^3$-fashion. Any of the three $sp^2$ carbon atoms may be substituted with a hydrocarbyl, substituted hydrocarbyl, heteroatom connected hydrocarbyl, heteroatom connected substituted hydrocarbyl, or O-silyl group. Examples of π-allyl groups include:

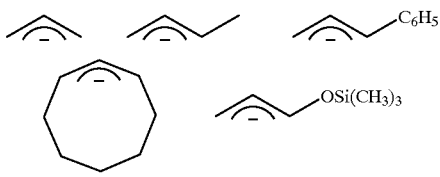

The term π-benzyl group denotes a π-allyl group where two of the sp² carbon atoms are part of an aromatic ring. Examples of π-benzyl groups include:

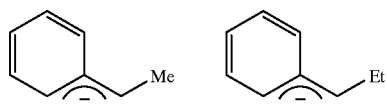

As used herein, the terms "monomer" and "olefin monomer" refer to the olefin or other monomer compound before it has been polymerized; the term "monomer units" refers to the moieties of a polymer that correspond to the monomers after they have been polymerized.

In some cases, a compound D is required as a cocatalyst. Suitable compounds D include a neutral Lewis acid capable of abstracting Q⁻ or W⁻ to form a weakly coordinating anion, a cationic Lewis acid whose counterion is a weakly coordinating anion, or a Bronsted acid whose conjugate base is a weakly coordinating anion. Preferred compounds D include: methylaluminoxane (hereinafter MAO) and other aluminum sesquioxides, $R^{40}{}_3Al$, $R^{40}{}_2AlCl$, $R^{40}AlCl_2$ (wherein $R^{40}$ is alkyl), organoboron compounds, boron halides, $B(C_6F_5)_3$, $R^{41}{}_3Sn[BF_4]$ (wherein $R^{41}$ hydrocarbyl), $MgCl_2$, and $H^+J^-$, wherein $J^-$ is a weakly coordinating anion. Examples of $H^+J^-$ are the ether solvate of hydrogen tetrakis [3,5-bis(trifluoromethyl)phenyl]borate and montmorillinite clay.

Examples of "solid support" include inorganic oxide support materials, such as: talcs, silicas, titania, silica/chromia, silica/chromia/titania, silica/alumina, zirconia, aluminum phosphate gels, silanized silica, silica hydrogels, silica xerogels, silica aerogels, montmorillonite clay and silica co-gels as well as organic solid supports such as polystyrene and functionalized polystyrene. (See, for example, Roscoe, S. B.; Frechet, J. M. J.; Walzer, J. F.; Dias, A. J.; "Polyolefin Spheres from Metallocenes Supported on Non-Interacting Polystyrene", 1998, Science, 280, 270–273 (1998).) An especially preferred solid support is one which has been pre-treated with D compounds as described herein, most preferably with MAO. Thus, in a preferred embodiment, the catalysts of the present invention are attached to a solid support (by "attached to a solid support" is meant ion paired with a component on the surface, adsorbed to the surface or covalently attached to the surface) which has been pre-treated with a compound D. Alternatively, the catalyst, the compound D, and the solid support can be combined in any order, and any number of D compounds can be utilized; in addition, the supported catalyst thus formed, may be treated with additional quantities of compound(s) D. In an especially preferred embodiment, the compounds of the present invention are attached to silica which has been pre-reated with MAO. Such supported catalysts are prepared by contacting the transition metal compound, in a substantially inert solvent—by which is meant a solvent which is either unreactive under the conditions of catalyst preparation, or if reactive, acts to usefully modify the catalyst activity or selectivity—with MAO treated silica for a sufficient period of time to generate the supported catalysts. Examples of substantially inert solvents include toluene, mineral spirits, hexane, $CH_2Cl_2$ and $CHCl_3$.

As noted above, it is preferred that certain of the compounds of the present invention be attached to a solid support which has been pre-treated with a compound D or mixed with D in any order. Preferred D groups include methylaluminoxane (hereinafter MAO) and other aluminum sesquioxides, $R^{70}{}_3Al$, $R^{70}{}_2AlCl$, $R^{70}AlCl_2$ (where $R^{70}$ is alkyl), organoboron compounds, boron halides, $B(C_6F_5)_3$, $BPh_3$, and $B(3,5\text{-}(CF_3)_2C_6H_3)_3$.

Preferred olefins useful in the practice of the processes of the present invention include ethylene and α-olefins such as propylene, 1-butene, 1-hexene, 1-octene, ethyl undecenoate and cyclic olefins such as cyclopentene.

When the polymerizations are conducted in the liquid phase, said liquid phase may include solvent or neat monomer. The molar ratio of neutral Lewis acid to transition metal complex can be from 1 to 10000, preferably 10 to 1000. The pressure at which the ethylene polymerizations and copolymerizations take place can be from 1 atmosphere to 1000 atmospheres, preferably 1 to 100 atmospheres.

While not wishing to be bound by theory, the present inventors believe that the Lewis acid (e.g. alkyl aluminum species such as trimethylaluminum or MAO) may be acting to further activate the catalysts provided herein via coordination to one or more of those heteroatoms which are not directly bound to the transition metal M, but which are π-conjugated to the nitrogens which are bound to the transition metal M. Substituents which contain additional Lewis basic groups, including, but not limited to, methoxy groups, positioned so as to further promote the binding of the Lewis acid at such π-conjugated heteroatoms, are also included in this invention. A nonlimiting example of secondary Lewis acid binding would include the following:

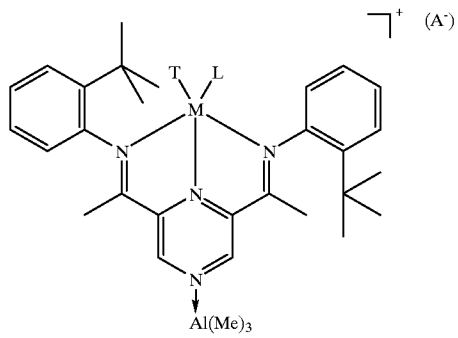

Wherein,

T is H, hydrocarbyl, substituted hydrocarbyl, or other group capable of inserting an olefin;

L is H, hydrocarbyl, substituted hydrocarbyl, hydroxide, alkoxide, an olefin or a neutral base where the donating atom is nitrogen, oxygen, or sulfur capable of being displaced by an olefin; in addition, T and L may be taken together to form, for example, a π-allyl or a π-benzyl group;

M is Co(II), Co(III), Fe(II), Fe(III), Ru(II), Ru(III), Mn(II) or Mn(III); and

A⁻ is a weakly coordinating anion.

The polymerizations may be conducted as solution polymerizations, as non-solvent slurry type polymerizations, as slurry polymerizations using one or more of the olefins or other solvent as the polymerization medium, or in the gas phase. One of ordinary skill in the art, with the present disclosure, would understand that the catalyst could be supported using a suitable solid support and methods known in the art. Substantially inert solvents, such as toluene, hydrocarbons, methylene chloride and the like, may be used. Propylene and 1-butene are excellent monomers for use in slurry-type copolymerizations and unused monomer can be flashed off and reused.

Temperature and olefin pressure have significant effects on polymer structure, composition, and molecular weight. Suitable polymerization temperatures are preferably from about −100° C. to about 200° C., more preferably in the 20° C. to 150° C. range.

After the reaction has proceeded for a time sufficient to produce the desired polymers, the polymer can be recovered from the reaction mixture by routine methods of isolation and/or purification.

In general, the polymers of the present invention are useful as components of thermoset materials, as elastomers, as packaging materials, films, compatibilizing agents for polyesters and polyolefins, as a component of tackifying compositions, and as a component of adhesive materials.

High molecular weight resins are readily processed using conventional extrusion, injection molding, compression molding, and vacuum forming techniques well known in the art. Useful articles made from them include films, fibers, bottles and other containers, sheeting, molded objects and the like.

Low molecular weight resins are useful, for example, as synthetic waxes and they may be used in various wax coatings or in emulsion form. They are also particularly useful in blends with ethylene/vinyl acetate or ethylene/methyl acrylate-type copolymers in paper coating or in adhesive applications.

Although not required, typical additives used in olefin or vinyl polymers may be used in the new homopolymers and copolymers of this invention. Typical additives include pigments, colorants, titanium dioxide, carbon black, antioxidants, stabilizers, slip agents, flame retarding agents, and the like. These additives and their use in polymer systems are known per se in the art.

The molecular weight data presented in the following examples is determined at 135° C. in 1,2,4-trichlorobenzene using refractive index detection, calibrated using narrow molecular weight distribution poly(styrene) standards.

EXPERIMENTAL SECTION

Example 1

Preparation of the Cobalt Dichloride Complex of 2, 5-bis(5-tert-butyl-2-benzoxazolyl)thiophene Under an inert argon atmosphere, a flask that had previously been heated to 200° C. for several hours and allowed to cool to room temperature under vacuum was charged with cobalt dichloride (59.6 mg; 0.459 mmol). A solution of 2,5-bis(5-tert-butyl-2-benzoxazolyl)thiophene (201.4 mg; 0.468 mmol) was dissolved in 5 mL tetrahydrofuran and added to cobalt dichloride. The suspension was stirred at room temperature for 6 days. The resulting mixture was filtered. The filtrate was concentrated to dryness under vacuum to afford 297 mg of solid.

Example 2

Polymerization of Ethylene with the Cobalt Dichloride Complex of 2,5-bis(5-tert-butyl-2-benzoxazolyl)thiophene A 250-mL pear shaped Schlenk flask, previously heated to 200° C. for several hours and allowed to cool to room temperature under vacuum, was charged under an argon inert atmosphere with the cobalt dichloride complex of 2,5-bis(5-tert-butyl-2-benzoxazolyl)thiophene (6.4 mg; 11 μmol) and equipped with a rubber septum and a magnetic stirring bar. Anhydrous toluene (50 mL) was added. The inert atmosphere was then replaced by 1 atm ethylene. After stirring the solution under ethylene for 5 min, 1.9 mL of a 10 wt % methylaluminoxane in toluene was added. The resulting solution was stirred vigorously under 1 atm ethylene for 15 min and then quenched with methanol, acetone and 6 M hydrochloric acid. An organic work-up led to 98.2 mg oligomers of ethylene ($MW_{peak}$ as determined by Field-Desorption Mass Spectrometry: 336).

Example 3

Preparation of the Cobalt Dichloride Complex of 2, 6-bis[(4S)-isopropyl)-2-oxazolin-2-yl]pyridine Under an inert argon atmosphere, a flask that had previously been heated to 200° C. for several hours and allowed to cool to room temperature under vacuum was charged with cobalt dichloride (53.5 mg; 0.412 mmol). A solution of 2,6-bis[(4S)-isopropyl)-2-oxazolin-2-yl]pyridine (127.0 mg; 0.421 mmol) in tetrahydrofuran was added to cobalt dichloride. The suspension was stirred at room temperature for 6 days. Dichloromethane (5 mL) was added to the suspension and the resulting mixture was filtered. The filtrate was concentrated to dryness under vacuum to afford 137 mg of a jade-green solid.

Example 4

Polymerization of Ethylene with the Cobalt Dichloride Complex of 2,6-bis[(4S)-isopropyl)-2-oxazolin-2-yl]pyridine A 250-mL pear shaped Schlenk flask, previously heated to 200° C. for several hours and allowed to cool to room temperature under vacuum, was charged under an argon inert atmosphere with the cobalt dichloride complex of 2,6-bis[(4S)-isopropyl)-2-oxazolin-2-yl]pyridine (5.9 mg; 14 μmol) and equipped with a rubber septum and a magnetic stirring bar. Anhydrous toluene (50 mL) was added. The inert atmosphere was then replaced by 1 atm ethylene. After stirring the solution for a few minutes, 2.3 mL of a 10 wt % methylaluminoxane in toluene was added. The resulting solution was stirred vigorously under 1 atm ethylene for 10 min and then quenched with methanol, acetone and 6 M hydrochloric acid. An organic work-up led to 282.3 mg oligomers of ethylene ($MW_{peak}$ as determined by Field-Desorption Mass Spectrometry: 336).

Example 5

Preparation of the Cobalt Dichloride Complex of 2, 6-bis(2-benzimidazolyl)pyridine Under an inert argon atmosphere, a 20-mL scintillation vial that had previously been heated to 200° C. for several hours and allowed to cool to room temperature under vacuum was charged with cobalt dichloride (14.5 mg; 0.111 mmol) and 2 mL THF. A suspension of 2,6-bis(2-benzimidazolyl)pyridine (34.7 mg; 0.111 mmol) in tetrahydrofuran (8 mL) was added to cobalt dichloride. The suspension was stirred at room temperature for 1 day. The volatiles were removed in vacuo and the solid used as is.

Example 6

Polymerization of Ethylene Using the Cobalt Dichloride Complex of 2,6-bis(2-benzimidazolyl) pyridine A 250-mL pear shaped Schlenk flask, previously heated to 200° C. for several hours and allowed to cool to room temperature under vacuum, was charged under an argon inert atmosphere with the cobalt dichloride complex of 2,6-bis(2-benzimidazolyl) (5.7 mg; 13 μmol) and equipped with a rubber septum and a magnetic stirring bar. Anhydrous toluene (50 mL) was added. The inert atmosphere was then replaced by 1 atm ethylene and 4.5 mL of a 10 wt % methylaluminoxane in toluene was added. The resulting solution was stirred vigorously under 1 atm ethylene for 25 min and then quenched with methanol, acetone and 6 M hydrochloric acid. An organic work-up led to 196.2 mg oligomers of ethylene ($MW_{peak}$ as determined by Field-Desorption Mass Spectrometry: 336).

Example 7

Synthesis of Tris(6-Bromo-2-Pyridyl)Phosphine

A solution of n-BuLi in hexanes (2.5 M, 1.67 mL, 4.2 mmol) was added dropwise to a suspension of 2,6-dibromopyridine (1.0 g, 4.2 mmol) in diethyl ether (7.5 mL) at −78° C. The resulting orange solution was stirred at −78° C. for 10 min, then treated with a solution of $PCl_3$ (123 μL, 1.4 mmol) dissolved in diethyl ether (0.25 mL). The resulting dark red suspension was stirred for four hours while the temperature was allowed to rise to −25° C. The reaction was quenched with 2 N HCl (1.03 mL), and filtered. The solid residue was crystallized from boiling o-xylene, rinsed with acetone and dried in vacuo to afford a crude mixture (254 mg) containing tris(5-bromo-2-pyridyl)phosphine and tris (5-bromo-2-pyridyl)phosphine oxide, which was not purified further.

Example 8

Synthesis of Tris(6-Bromo-2-Pyridyl)Phosphine Oxide

A suspension of a mixture of tris(6-bromo-2-pyridyl) phosphine and tris(6-bromo-2-pyridyl)phosphine oxide (148.2 mg, 0.295 mmol based on tris(6-bromo-2-pyridyl) phosphine) in acetone (1.2 mL) was treated with a 30% aqueous solution of $H_2O_2$ (1.6 mL) at room temperature. The rsulting suspension was stirred at rt for 2 days, then concentrated in vacuo to afford tris(6-bromo-2-pyridyl) phosphine oxide (160.2 mg, >100%) contaminated with $H_2O$. The residue was dissolved in $CH_2Cl_2$ and concentrated in vacuo to remove some of the residual $H_2O$: $^1H$ NMR (300 MHz, $CDCl_3$) δ 8.12–8.16 (m, 1 H), 7.72–7.79 (m, 1 H), 7.62–7.65 (m, 1 H); FDMS m/z (relative intensity) 515 ($M^+$, 35%), 517 (($M+2$)$^+$, 100%), 519 (($M+4$)$^+$, 99%), 521 (($M+6$)$^+$, 34%).

Example 9

Preparation of the Cobalt Dichloride Complex of tris(6-Bromo-2-Pyridyl)phosphine Oxide Under an inert argon atmosphere, a 20-mL scintillation vial that had previously been heated to 200° C. for several hours and allowed to cool to room temperature under vacuum was charged with cobalt dichloride (4.5 mg; 35 μmol). A solution of tris(6-bromo-2-pyridyl)phosphine oxide (18.1 mg; 34.9 μmol) in THF (10 mL) was added to the cobalt salt. The suspension was stirred for 1 day at room temperature. The volatiles were then removed in vacuo and the blue solid used as is for polymerization of ethylene.

Example 10

Polymerization of Ethylene Using the Cobalt Dichloride Complex of tris(6-bromopyrid-2-yl) phosphine Oxide A 250-mL pear shaped Schlenk flask, previously heated to 200° C. for several hours and allowed to cool to room temperature under vacuum, was charged under an argon inert atmosphere with the cobalt dichloride complex of tris(6-bromopyrid-2-yl)phosphine oxide (4.2 mg; 6.5 μmol) and equipped with a rubber septum and a magnetic stirring bar. Anhydrous toluene (50 mL) was added. The inert atmosphere was then replaced by 1 atm ethylene and 3.0 mL of a 10 wt % methylaluminoxane in toluene was added. Some particulates did not dissolve completely in the solution. The resulting mixture was stirred vigorously under 1 atm ethylene for 15 min and then quenched with methanol, acetone and 6 M hydrochloric acid. An organic work-up led to 190 mg oligomers of ethylene.

We claim:

1. A process for the preparation of polyolefins, which comprises contacting one or more monomers of the formula R'CH=CHR" with a transition metal complex of the formula (I):

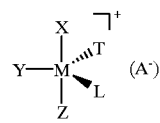

wherein R', R" are H, hydrocarbyl or substituted hydrocarbyl, and may be linked to form a cyclic olefin;

M is Co(II), Co(III), Fe(II), Fe(III), Ru(II), Ru(III), Mn(II) or Mn(III);

T is H, hydrocarbyl, substituted hydrocarbyl, or other group capable of inserting an olefin;

L is an olefin or a neutral base, said base having a donating atom, where the donating atom is nitrogen, oxygen, or sulfur capable of being displaced by an olefin; in addition, T and L may be taken together to form a π-allyl or a π-benzyl group;

$A^-$ is a weakly coordinating anion; and

X, Y, and Z are selected from various functional groups or combinations of such functional groups selected from the group consisting of

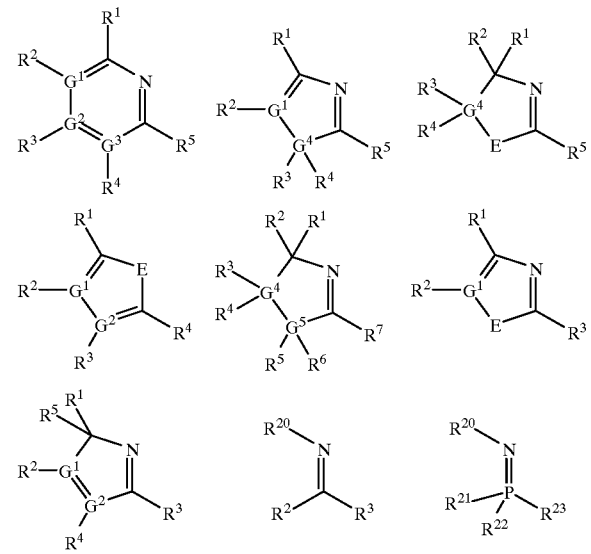

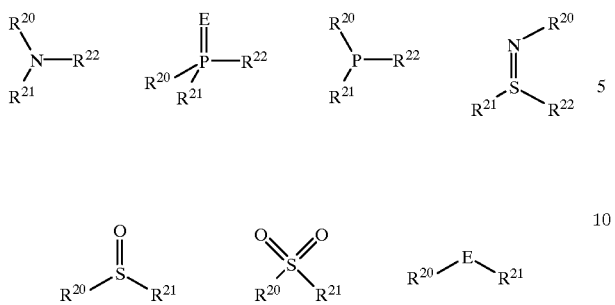

wherein $R^1, R^2, R^3, R^4, R^5, R^6, R^7$ are each independently H, hydrocarbyl, substituted hydrocarbyl, a heteroatom connected monoradical wherein the connected heteroatom is selected from the group consisting of elements of Group 15 and 16, and silicon, and may also be linked by a bridging hydrocarbyl group or to one another or to $R^{20}$–$R^{23}$ to form a covalent bond;

$R^{20}$, $R^{21}$, $R^{22}$ and $R^{23}$ are each independently hydrocarbyl, substituted hydrocarbyl or silyl, and may also be linked to $R^1$–$R^7$ to form a covalent bond;

E is either O or S;

$G^1$, $G^2$, and $G^3$ are independently C or N, provided that when $G^1$, $G^2$, and $G^3$ are N, only hydrocarbyl and substituted hydrocarbyl substituents are covalently bound to N, and further provided that the octet rule is satisfied in said atom;

$G^4$ and $G^5$ are independently C, N, O, or S, provided that when they are O, N, and S, only hydrocarbyl and substituted hydrocarbyl substituents are covalently bound to O, N or S, and further provided that the octet rule is satisfied in said atom;

further provided that X, Y and Z are taken together to form groups of a formula other than the formula

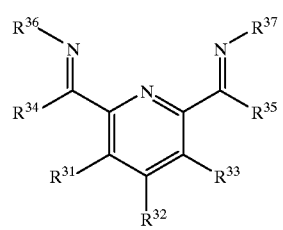

wherein $R^{31}$, $R^{32}$, $R^{33}$, $R^{34}$ and $R^{35}$ are each independently H, hydrocarbyl, substituted hydrocarbyl, heterohydrocarbyl, or substituted heterohydrocarbyl, or an inert functional group; and $R^{36}$ and $R^{37}$ are aryl, substituted aryl, H, halogen, hydrocarbyl, substituted hydrocarbyl, heterohydrocarbyl, or substituted heterohydrocarbyl.

2. The process of claim 1, wherein X, Y, and Z are taken together to form a group selected from the group consisting of

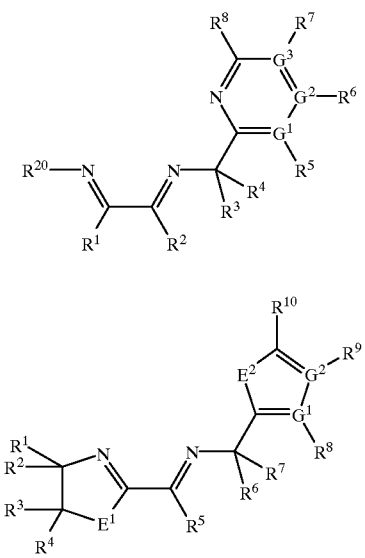

C

CI

CII

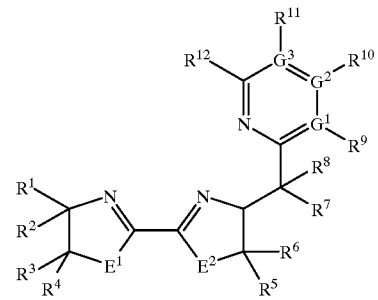

CIII

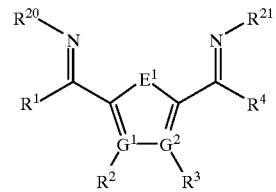

CIV

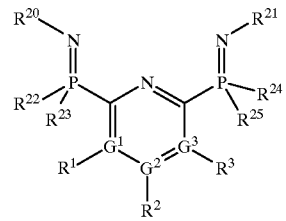

CV

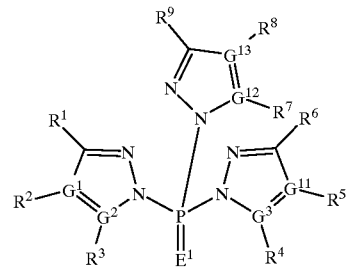

-continued

CVII 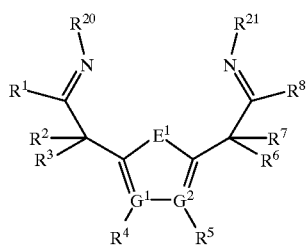

CVIII 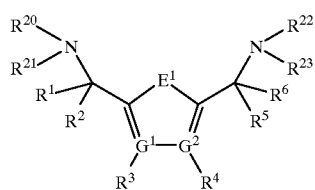

CIX 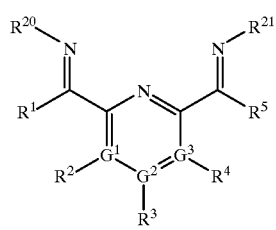

CXI 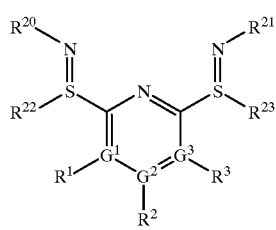

CXII 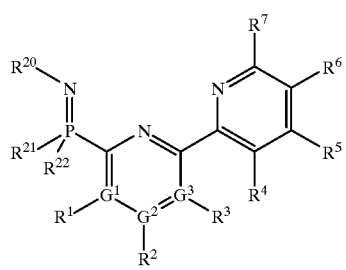

CXIII 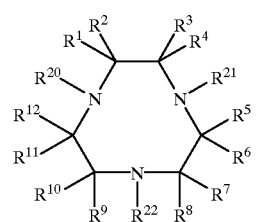

-continued

CXIV 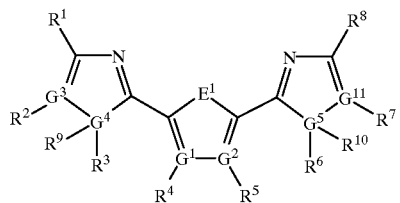

CXV 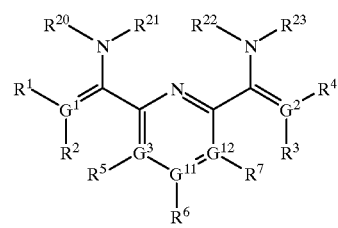

CXVI 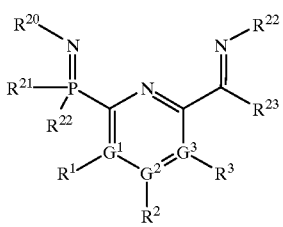

wherein $R^1$–$R^{15}$ are each independently H, hydrocarbyl, substituted hydrocarbyl, a heteroatom connected monoradical wherein the connected heteroatom is selected from the group consisting of elements of Group 15 and 16, and silicon, and may also be linked by a bridging hydrocarbyl group or to one another or to $R^{20}$–$R^{23}$ to form a covalent bond;

$R^{20}$, $R^{21}$, $R^{22}$, $R^{23}$, $R^{24}$, and $R^{25}$ are each independently hydrocarbyl, substituted hydrocarbyl or silyl, and may also be linked to $R^1$–$R^7$ to form a covalent bond;

and $E^1$ and $E^2$ are each independently either O or S;

$G^1$, $G^2$, $G^3$, $G^{11}$, $G^{12}$ and $G^{13}$ are each independently C or N, provided that when they are N, only hydrocarbyl and substituted hydrocarbyl substituents are covalently bound to N, and further provided that the octet rule is satisfied in said atom;

$G^4$ and $G^5$ are each independently C, N, O, or S, provided that when $G^4$ and $G^5$ are O, N, and S, only hydrocarbyl and substituted hydrocarbyl substituents are covalently bound to O, N or S, and further provided that the octet rule is satisfied in said atom.

3. The process of claim 1, wherein at least one of X, Y and Z is

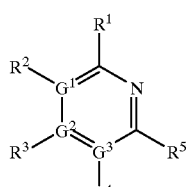

while the remaining of X, Y, and Z are:

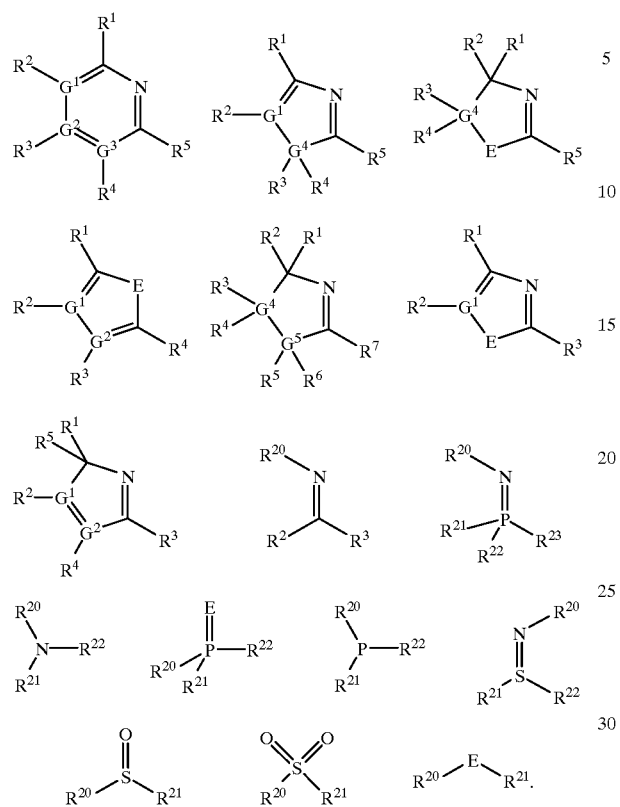

4. The process of claim 1, wherein M is Co(II), Fe(II), Ru(II), or Mn(II).

5. The process of claim 1, wherein M is Co(II) or Fe(II).

6. The process of claim 1, wherein X, Y and Z are taken together to form a group of the formula

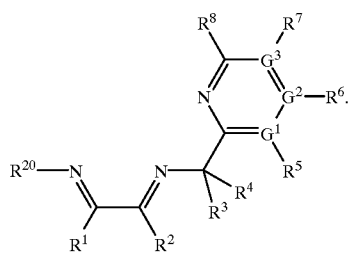

7. The process of claim 1, wherein X, Y and Z are taken together to form a group of the formula

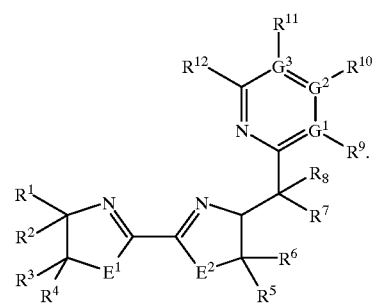

8. The process of claim 1, wherein X, Y and Z are taken together to form a group of the formula

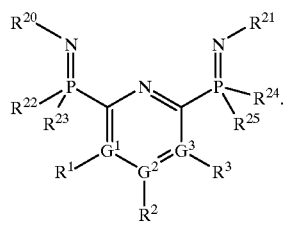

9. The process of claim 1, wherein X, Y and Z are taken together to form a group of the formula

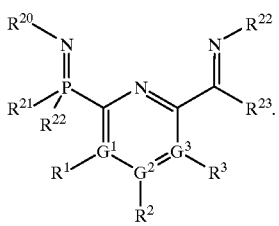

10. The process of claim 1, wherein X, Y and Z are taken together to form a group of the formula

CIX

11. The process of claim 1, wherein X, Y and Z are taken together to form a group of the formula

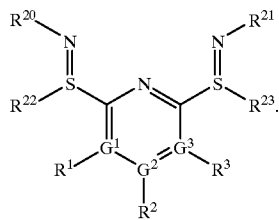

CXI

12. The process of claim 1, wherein X, Y and Z are taken together to form a group of the formula

CXII

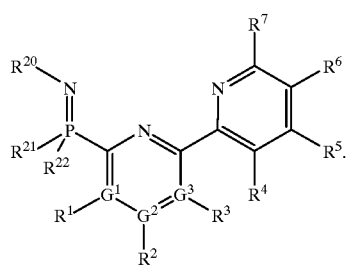

13. The process of claim 1, wherein X, Y and Z are taken together to form a group of the formula

CXV

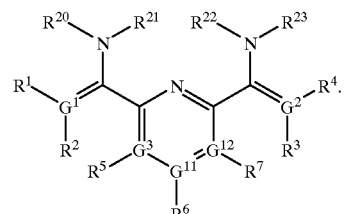

14. The process of claim 1, wherein the transition metal complex of formula (I) is attached to a solid support.

15. The process of claim 14, wherein the solid support is silica.

16. A process for the polymerization of olefins which comprises contacting one or more monomers of the formula R'CH=CHR" with a transition metal catalyst, wherein said catalyst is formed by combining a first compound D, which is a neutral Lewis acid that is capable of abstracting $Q^-$ or $W^-$ to form a weakly coordinating anion, or a cationic Lewis acid whose counterion is a weakly coordinating anion, or a Brønsted acid whose conjugate base is a weakly coordinating anion, with a second compound of the formula (II):

II

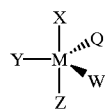

wherein R', R" are H, hydrocarbyl or substituted hydrocarbyl, and may be linked to form a cyclic olefin;

Q is hydrocarbyl, chloride, iodide, bromide, substituted hydrocarbyl, hydroxide, alkoxide, amide, nitrate or sulphonate or other group capable of being abstracted by compound D, which is a neutral Lewis acid that is capable of abstracting $Q^-$ or $W^-$ to form a weakly coordinating anion, or a cationic Lewis acid whose counterion is a weakly coordinating anion, or a Brønsted acid whose conjugate base is a weakly coordinating anion;

W is hydrocarbyl, chloride, iodide, bromide, substituted hydrocarbyl, hydroxide, alkoxide, amide, nitrate or sulphonate or other group capable of inserting an olefin;

M is Co(II), Co(III), Fe(II), Fe(III), Ru(II), Ru(III), Mn(II) or Mn(III); and

X, Y, and Z are selected from various functional groups or combinations of such functional groups selected from the group consisting of

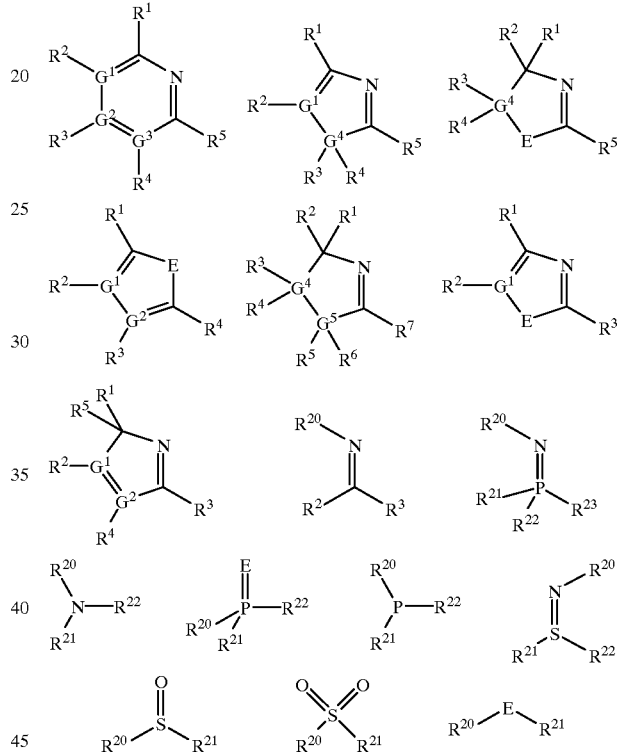

wherein $R^1, R^2, R^3, R^4, R^5, R^6, R^7$ are each independently H, hydrocarbyl, substituted hydrocarbyl, a heteroatom connected monoradical wherein the connected heteroatom is selected from the group consisting of elements of Group 15 and 16, and silicon, and may also be linked by a bridging hydrocarbyl group or to one another or to $R^{20}$–$R^{23}$ to form a covalent bond;

$R^{20}$, $R^{21}$, $R^{22}$, and $R^{23}$ are each independently hydrocarbyl, substituted hydrocarbyl or silyl, and may also be linked to $R^1$–$R^7$ to form a covalent bond;

E is either O or S;

$G^1$, $G^2$, and $G^3$ are independently C or N, provided that when they are N, only hydrocarbyl and substituted hydrocarbyl subtituents are covalently bound to N, and further provided that the octet rule is satisfied in said atom; And $G^4$ and $G^5$ are independently C, N, O, or S, provided that when they are O, N, and S, only hydrocarbyl and substituted hydrocarbyl substituents are covalently bound to O, N or S, and further provided that the octet rule is satisfied in said atom;

further provided that X, Y and Z are taken together to form groups of a formula other than the formula

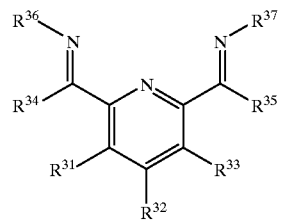

wherein $R^{31}$, $R^{32}$, $R^{33}$, $R^{34}$ and $R^{35}$ are each independently H, hydrocarbyl, substituted hydrocarbyl, heterohydrocarbyl, or substituted heterohydrocarbyl, or an inert functional group; and $R^{36}$ and $R^{37}$ are aryl, substituted aryl, H, halogen, hydrocarbyl, substituted hydrocarbyl, heterohydrocarbyl, or substituted heterohydrocarbyl.

17. The process of claim 16, wherein X, Y, and Z are taken together to form a group selected from the group consisting of

C

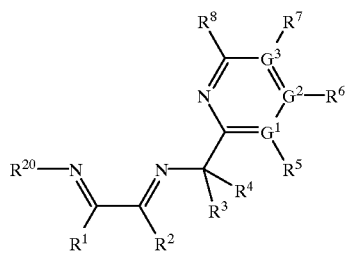

CI

CII

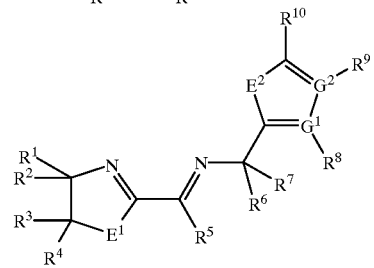

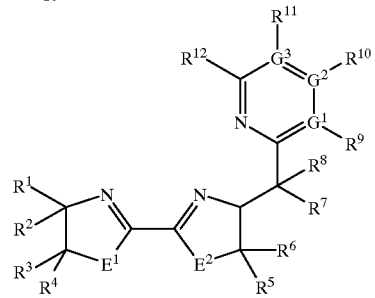

CIII

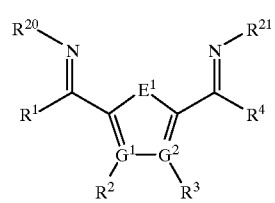

CIV

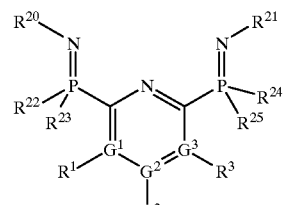

CV

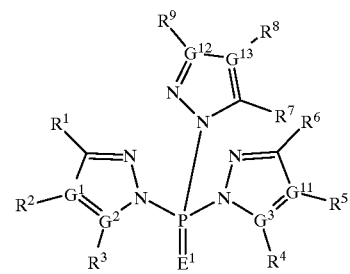

CVII

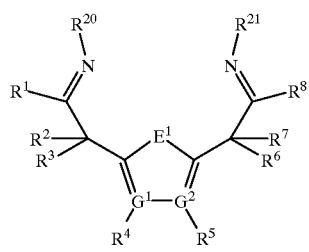

CVIII

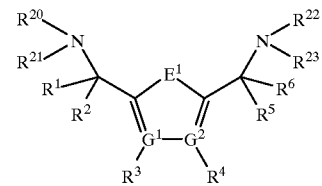

CIX

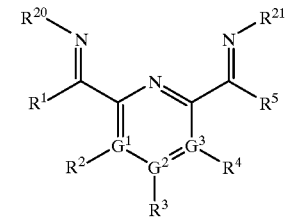

CXI

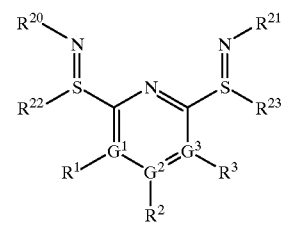

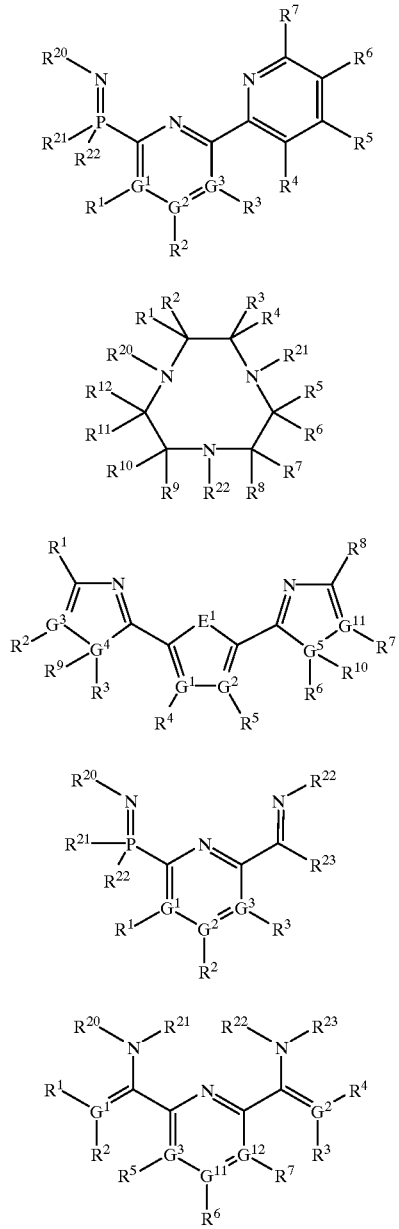

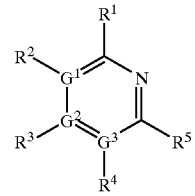

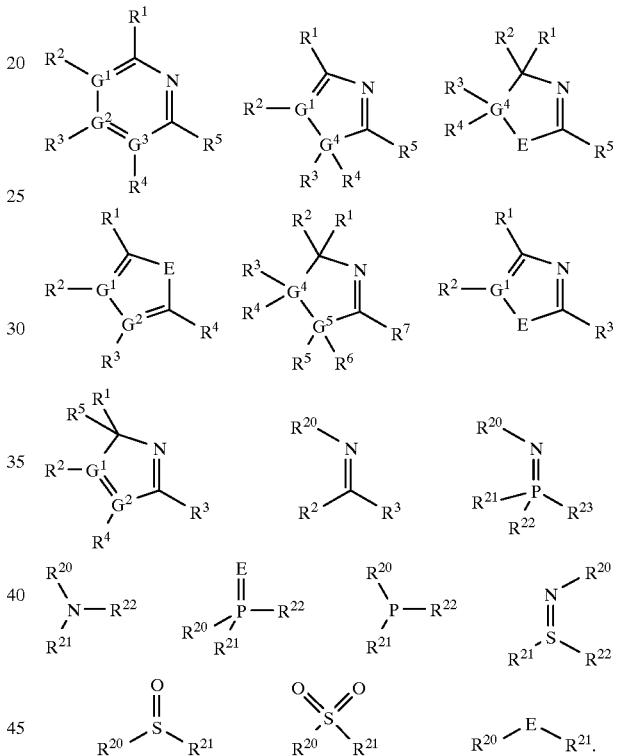

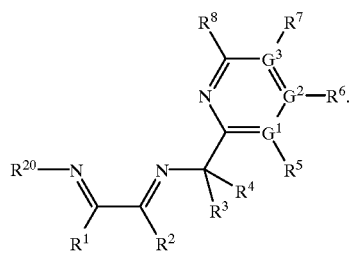

wherin R¹–R¹⁵ are each independently H, hydrocarbyl, substituted hydrocarbyl, a heteroatom connected monoradical wherein the connected heteroatom is selected from the group consisting of elements of Group 15 and 16, and silicon, and may also be linked to one another or to R²⁰–R²⁵ to form a covalent bond;

R²⁰–R²⁵ are each independently hydrocarbyl, substituted hydrocarbyl or silyl; and may also be linked to R¹–R⁷ to form a covalent bond;

and E¹ and E² are each independently either O or S;

G¹, G², G³, G¹¹, G¹² and G¹³ are each independently C or N, provided that when they are N, only hydrocarbyl and substituted hydrocarbyl subtituents are covalently bound to N, and further provided that the octet rule is satisfied in said atom;

G⁴ and G⁵ are each independently C, N, O, or S, provided that when they are O, N, and S, only hydrocarbyl and substituted hydrocarbyl substituents are covalently bound to O, N or S, and further provided that the octet rule is satisfied in said atom.

18. The process of claim 16, wherein at least one of X, Y and Z is while the other of X, Y, and Z is:

19. The process of claim 16, wherein M is Co(II), Fe(II), Ru(II), or Mn(II).

20. The process of claim 16, wherein M is Co(II) or Fe(II).

21. The process of claim 16, wherein X, Y and Z are taken together to form a group of the formula 22. The process of claim 16, wherein X, Y and Z are taken together to form a group of the formula

23. The process of claim 16, wherein X, Y and Z are taken together to form a group of the formula

CII

24. The process of claim 16, wherein X, Y and Z are taken together to form a group of the formula

CIV

25. The process of claim 16, wherein X, Y and Z are taken together to form a group of the formula

CIX

26. The process of claim 16, wherein X, Y and Z are taken together to form a group of the formula

CXI

27. The process of claim 16, wherein X, Y and Z are taken together to form a group of the formula

28. The process of claim 16, wherein X, Y and Z are taken together to form a group of the formula

CXII

29. The process of claim 16, wherein the transition metal complex of formula (II) is attached to a solid support.

30. The process of claim 29, wherein the solid support is silica.

31. The process of claim 30, wherein the silica has been pretreated with a compound D selected from the group consisting of methylaluminoxane, and other aluminum sesquioxides of the formulas $R^{40}_3Al$, $R^{40}_2AlCl$, and $R^{40}AlCl_2$, wherein $R^{40}$ is alkyl, organoboron compounds, boron halides, $B(C_6F_5)_3$, $BPh_3$, and $B(3,5-(CF_3)_2C_6H_3)_3$.

32. The process of claim 31, wherein the compound D is methylaluminoxane.

33. The process of claim 1, wherein X, Y, and Z are taken together to form a group selected from compounds

C

CXV

CXVI

CIX

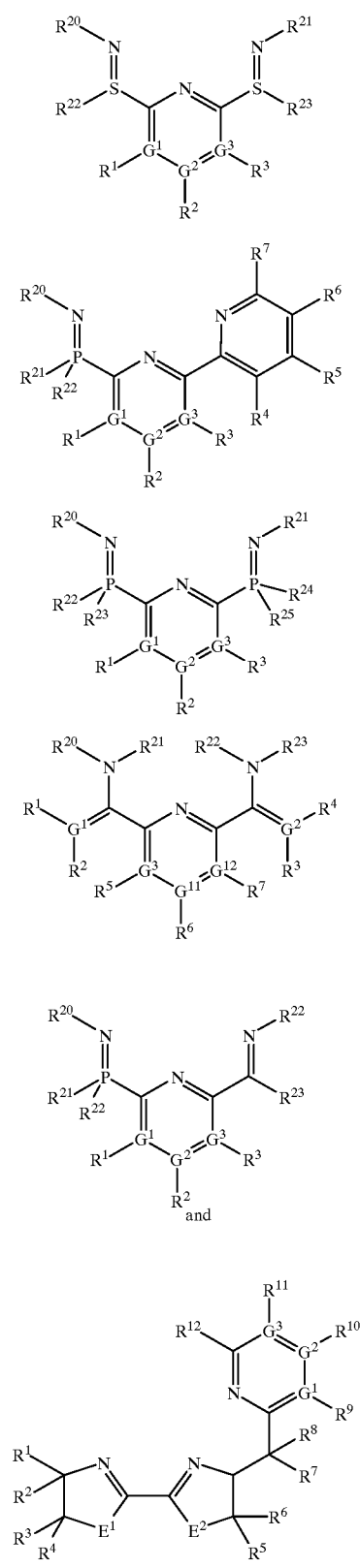
34. The process of claim 17, wherein X, Y, and Z are taken together to form a group selected from compounds -continued
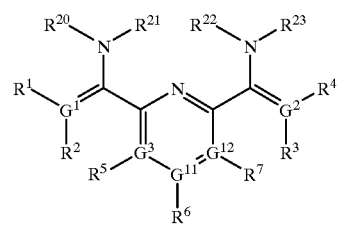
CXV
and
-continued
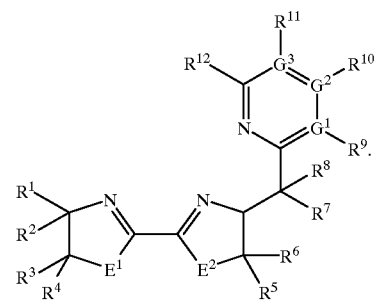
CII
* * * * *